(12) United States Patent
Shurtleff et al.

(10) Patent No.: US 9,940,214 B2
(45) Date of Patent: Apr. 10, 2018

(54) INDEX FILTER FOR VISUAL MONITORING

(71) Applicant: CISCO TECHNOLOGY, INC., San Jose, CA (US)

(72) Inventors: Mark Stephan Shurtleff, Oakland, CA (US); Wenhui Yu, Sunnyvale, CA (US)

(73) Assignee: Cisco Technology, Inc., San Jose, CA (US)

( * ) Notice: Subject to any disclaimer, the term of this patent is extended or adjusted under 35 U.S.C. 154(b) by 826 days.

(21) Appl. No.: 14/473,969

(22) Filed: Aug. 29, 2014

(65) Prior Publication Data

US 2016/0062866 A1 Mar. 3, 2016

(51) Int. Cl.
*G06F 11/30* (2006.01)
*G06F 19/00* (2018.01)
*H04L 12/26* (2006.01)

(52) U.S. Cl.
CPC ...... *G06F 11/3065* (2013.01); *G06F 19/3406* (2013.01); *G06F 19/3431* (2013.01); *H04L 43/00* (2013.01)

(58) Field of Classification Search
CPC ............. G06F 11/3065; G06F 19/3406; G06F 19/3431
See application file for complete search history.

(56) References Cited

U.S. PATENT DOCUMENTS

| | | | |
|---|---|---|---|
| 8,001,488 B1* | 8/2011 | Lam | G06F 3/0238 345/156 |
| 8,286,080 B2 | 10/2012 | Tai et al. | |
| 8,446,381 B2* | 5/2013 | Molard | B60K 35/00 178/18.03 |
| 2004/0225530 A1 | 11/2004 | Bell | |
| 2008/0214904 A1* | 9/2008 | Saeed | A61B 5/0006 600/301 |
| 2010/0238175 A1 | 9/2010 | Gilbert | |
| 2011/0201902 A1 | 8/2011 | Shiga | |
| 2013/0030260 A1 | 1/2013 | Hale | |
| 2014/0279865 A1 | 9/2014 | Kumar et al. | |
| 2014/0289617 A1 | 9/2014 | Rajagopalan et al. | |

FOREIGN PATENT DOCUMENTS

| | | |
|---|---|---|
| WO | WO1998/016895 | 4/1998 |
| WO | WO2006/136972 | 12/2006 |

\* cited by examiner

*Primary Examiner* — Elias Desta
(74) *Attorney, Agent, or Firm* — Cindy Kaplan

(57) ABSTRACT

In one embodiment, a method includes receiving a plurality of measurements, each measurement associated with a different parameter, calculating an index based on the measurements, and generating a visual index display indicating the index, the visual index display comprising a first portion and a second portion, each portion configured for selection by a user. A first set of measurements is displayed when the first portion is selected and a second set of measurements is displayed when the second portion is selected. The first set of measurements is a subset of the second set of measurements. An apparatus and logic are also disclosed herein.

20 Claims, 5 Drawing Sheets

INDEX FILTER FOR VISUAL MONITORING

TECHNICAL FIELD

The present disclosure relates generally to visual display of index measures, and more specifically, to filtering visualization for index measures.

BACKGROUND

Technology advancements allow users to gain access to an increasingly large amount of measurement data obtained from many diverse sources. While this data is extremely useful, the large amount of information available also presents challenges. For example, it may be difficult for users to quickly review, diagnose, and make informed decisions when presented with all of the available data.

BRIEF DESCRIPTION OF THE FIGURES

Corresponding reference characters indicate corresponding parts throughout the several views of the drawings.

DESCRIPTION OF EXAMPLE EMBODIMENTS

Overview

Figure 1:
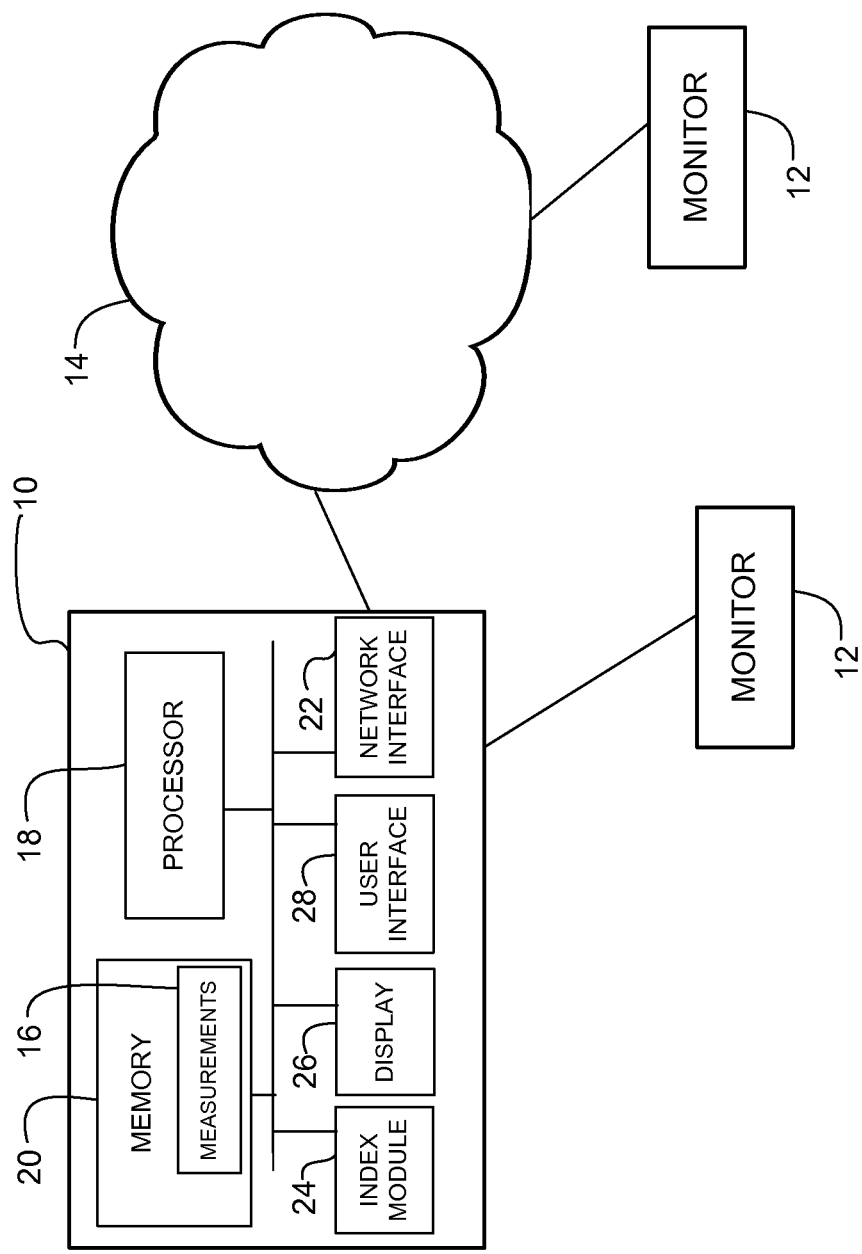
FIG. 1 illustrates an example of a network in which embodiments described herein may be implemented.

In one embodiment, a method generally comprises receiving a plurality of measurements, each measurement associated with a different parameter, calculating an index based on the measurements, and generating a visual index display indicating the index, the visual index display comprising a first portion and a second portion, each of the portions configured for selection by a user. A first set of measurements is displayed when the first portion is selected and a second set of measurements is displayed when the second portion is selected. The first set of measurements is a subset of the second set of measurements.

In another embodiment, an apparatus generally comprises a processor for calculating an index based on received measurements, each measurement associated with a different parameter, and generating a visual index display indicating the index, the visual index display comprising a first portion and a second portion, each portion configured for selection by a user. The apparatus further includes memory for storing the measurements. A first set of measurements is displayed when the first portion is selected and a second set of measurements is displayed when the second portion is selected. The first set of measurements is a subset of the second set of measurements.

Example Embodiments

The following description is presented to enable one of ordinary skill in the art to make and use the embodiments. Descriptions of specific embodiments and applications are provided only as examples, and various modifications will be readily apparent to those skilled in the art. The general principles described herein may be applied to other applications without departing from the scope of the embodiments. Thus, the embodiments are not to be limited to those shown, but are to be accorded the widest scope consistent with the principles and features described herein. For purpose of clarity, details relating to technical material that is known in the technical fields related to the embodiments have not been described in detail.

Index measures may be used to identify the health of various types of systems, devices, processes, or environments. For example, an index may be used to summarize measurements obtained via sensors in the environment or embedded in technology, or through monitoring processes or activities, to present an overall system, device, commodity, or environment state or health index. If one or more of the measurements (metrics) used to define an index is in an undesirable state then it may be important for the user to identify the parameter that is causing the index to fall outside of a specified range. The faster that the user can identify the problem, the faster the user can take action to identify and possibly correct the root cause.

In order to make the indexes easily accessible, the indexes may be graphically displayed. It is desirable to have critical indexes displayed in one place, and have them be clear, meaningful and up to date. Indexes may be shown for example, in a monitoring dashboard that provides tools for graphically presenting data. The dashboard may integrate and present information from multiple components or sources into a unified display. Based on these visual representations, a user may need to narrow down to a detailed page and view the individual measurements in a table, for example. Alerts may also be displayed in a list, in which the user has to search to identify the contributing factors if a measurement falls outside a specified threshold.

With advances in sensors, software, and hardware, many more measurements are available to display. This results in rich indexes that are sensitive to many contributors, however, this also increases the complexity for end users in troubleshooting an out of tolerance index. Prompt efficient diagnosis and action are important to many systems. Faster reactions lead to increased productivity and safer environments.

The embodiments described herein provide contextual visualization filtering in which an image displays an overall index value based on any number of contributing factors (measurements/metrics) along with out of tolerance measurements shown for one or more parameters. As described in detail below, the user may select a portion of a visual index display in order to see specific contributors to the index. With conventional systems it may take a number of selections or user navigations to see leading contributors to an out of tolerance index. The embodiments described herein maximize user efficiency in diagnosing index abnormalities by providing quick access to a filtered view of the leading contributors.

In one embodiment, the user may select a portion of the image to only view the measurements that are out of tolerance (or a percentage of those measurements). The user may then select another portion of the image to view the entire set of measurements. Since the images may be configured to display only the most relevant information, the data can be presented on a single page thereby providing clear and concise information while negating page navigation or multiple inputs by the user. The embodiments allow users to maintain context by remaining on the same page to view the measurement data used to generate the index. Furthermore, users may be just one click away from viewing all measurement data to further assist understanding and troubleshooting. The visualization filtering described herein may be applied to a wide range of applications, including for example, health care, environmental measures, factory diagnostics, network monitoring (e.g., diagnostic data about network devices (e.g., server, router, switch, data center devices) and applications running on them, or any other network data), finance (e.g., NASDAQ index), engineering, Internet of Everything, and many others.

Referring now to the drawings, and first to FIG. 1, a network in which the embodiments described herein may be implemented is shown. For simplification only a small number of nodes are shown. A user network device 10 is in communication with one or more monitors 12. The network device 10 may be in direct communication with one or more monitors 12 via a wired or wireless connection, or in communication with one or more monitors within the network 14 or in communication therewith. One or more monitors 12 may also be integral with the network device 10.

The network 14 may include one or more networks (e.g., local area network, metropolitan area network, wide area network, satellite network, enterprise network, Internet, intranet, radio access network, public switched network, virtual private network, wireless network, or any other network). Communication paths between the user network device 10 and monitors 12 may include any number or type of intermediate nodes (e.g., routers, switches, gateways, or other network devices), which facilitate passage of data between the network devices.

The monitor 12 may be any type of sensor or measuring device. The monitor 12 may comprise, for example, a network monitor (e.g., operable to monitor bandwidth, jitter, latency, network traffic, network activity, etc.), network device monitor (e.g., operable to measure CPU (computer processing unit) usage, available memory, application usage, etc.), environmental sensor (e.g., operable to measure air pollutants, etc.), data monitor (e.g., operable to measure stock fluctuations), website monitor (e.g., operable to monitor usage, download/upload times), process monitor (e.g., operable to monitor process efficiency), performance monitor, or any other type of monitor, sensor, gauge, indicator, meter, measurement device, and the like.

The network device 10 may be any type of device or group of devices configured to receive measurements and generate a visual index display. The network device 10 may comprise, for example, a management station, personal computer (e.g., desktop computer), cellular phone, tablet, laptop, personal digital assistant, portable computing device, multimedia device, and the like. As described further below, the network device 10 is operable to receive, process, and store measurements. The network device 10 may also include remotely located devices (e.g., storage for the network device). The network device 10 may be in communication with a central collection device in communication with a plurality of monitors 12 located throughout the network 14 or a building (e.g., factory, home), or in direct communication with one or more monitors 12.

In one embodiment, the network device 10 is a programmable machine that may be implemented in hardware, software, or any combination thereof. The network device 10 includes one or more processor 18, memory 20, and network interface 22. In the example shown in FIG. 1, the network device 10 also includes an index module 24 configured to generate the visual index display, display 26 for displaying the images, and a user interface 28 (e.g., graphical user interface (GUI)) for use in receiving input from a user.

Memory 20 may be a volatile memory or non-volatile storage, which stores various applications, operating systems, modules, and data for execution and use by the processor 18. Measurements 16 may be stored in memory 20 using one or more data structures (e.g., database, table).

Logic may be encoded in one or more tangible media for execution by the processor 18. For example, the processor 18 may execute codes stored in a computer-readable medium such as memory 20. The computer-readable medium may be, for example, electronic (e.g., RAM (random access memory), ROM (read-only memory), EPROM (erasable programmable read-only memory)), magnetic, optical (e.g., CD, DVD), electromagnetic, semiconductor technology, or any other suitable medium. The computer-readable medium may be non-transitory.

The network interface 22 may comprise one or more interfaces (linecards, ports) for receiving signals or data or transmitting signals or data to other devices. The interface 22 may include, for example, an Ethernet interface or wireless interface for connection to a computer or network.

The index module 24 is operable to calculate an index based on received measurements and generate the visual index display. The index module 24 may comprise software, code, or any other mechanism configured to perform processes described herein.

The display 26 may comprise any type of display screen (e.g., LCD (liquid crystal display) screen, LED (light emitting diode) screen, plasma display, projected image screen, electronic ink, or any other suitable display screen.

The user interface 28 may comprise any type of interface configured to receive input from a user indicating what detail of measurements to display. For example, the user interface 28 may comprise a touchscreen displaying a graphical user interface for displaying a selectable image and receiving input from the user. The user interface 28 may also include input devices (e.g., button or other mechanism, mouse, microphone, etc.) for receiving user input. For example, the user interface 28 may include a keyboard (e.g., touchscreen or keys) for use in entering criteria for displaying measurements (e.g., sensitivity setting as described below).

It is to be understood that the network and network device 10 shown in FIG. 1 and described above is only an example and that different configurations of network devices or network topologies may be used without departing from the scope of the embodiments. For example, the network device 10 may further include any suitable combination of hardware, software, algorithms, processors, devices, components, or elements operable to facilitate the capabilities described herein As described in detail below, the visual index display indicates the index and one or more of the measurements that define the index. The measurements are each associated with a different parameter (e.g., network parameters such as memory, utilization, bandwidth, CPU, storage, etc., environmental parameters such as pollen, dust, pet dander, $CO_2$, ozone, etc., or any other parameter). The index may comprise, for example, a value calculated based on the measurements associated with the index, a description of the state of the system based on the calculated value (e.g., healthy, unhealthy, very unhealthy), or a color indicating the health of the system based on the calculated value (e.g., green, yellow, red). The index value may be calculated based on an average of all of the measurements (or variance from a defined threshold or average) or one or more of the measurements may be assigned a weight for use in calculating the overall index. The measurement may be a monitored (or averaged) value (e.g., temperature, parts per million, rate, delay, size, speed, etc.), a percentage (e.g., percent utilized, percent of capacity, percent above or below average value or threshold), an amount the measurement is out of tolerance (e.g., above or below a defined threshold). The measurement value may also be normalized so that different parameters can be compared to one another, as described below. It is to be understood that the indexes and measurements described herein are only examples and that the embodiments may be used to display other types of indexes and measurements, without departing from the scope of the embodiments.

The visual index display may be any type of image that indicates an overall index based on a plurality of individual (constitutes) measurements. In one embodiment, the visual index display comprises at least two selectable portions (user selection interfaces). A first set of measurements is displayed when the first portion is selected and a second set of measurements is displayed when the second portion is selected. The first set of measurements is a subset of the second set measurements so that a smaller number of measurements are shown to allow the user to easily identify the problem area (or areas) and make an informed decision about what the data is showing. For example, the first set of measurements may include all out of tolerance measurements (i.e., measurements outside of a specified threshold) or just a portion of the out of tolerance measurements (e.g., top X % of the out of tolerance measurements). As described below with respect to FIG. 5, a group comprising all out of tolerance measurements may be sorted and ranked based on the amount that the measurement is out of tolerance. A configured sensitivity level may then be used to determine how many of the out of tolerance measurements are shown when the first portion of the image is selected (e.g., top 10%, top 50%, top 3, top 10, etc.). The sensitivity may be set by the user (e.g., user configured percentile as described below).

The threshold may comprise, for example, a maximum value, minimum value, range, or amount (percent) above or below a specified value or average. The measurements may use the same threshold or one or more of the measurements may use a different threshold to account for variations in allowable tolerances for different parameters.

Figure 2A:
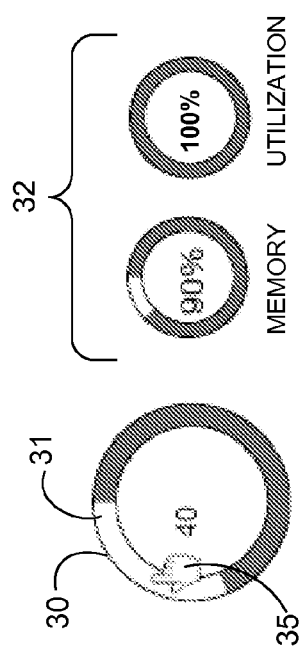
FIG. 2A depicts an example of a visual index display with a first portion of the display selected and out of tolerance measurements shown, in accordance with one embodiment.
Figure 2B:
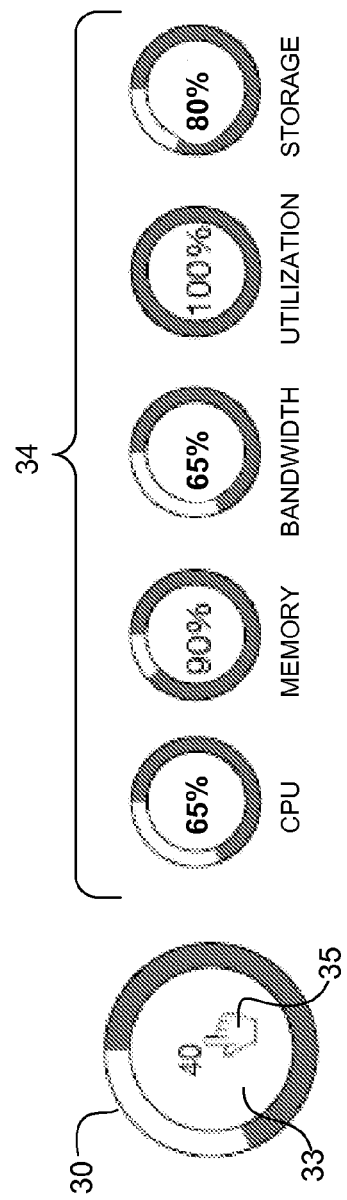
FIG. 2B depicts the visual index display of FIG. 2A with a second portion of the display selected and additional measurements shown, in accordance with one embodiment

In one embodiment, the visual index display comprises a gauge that is contextual when measurements are out of tolerance. FIGS. 2A and 2B illustrate an example of a visual index display, in accordance with one embodiment. It is to be understood that this is only an example and that other images, shapes, configurations, or arrangements may be used to display the index and one or more measurements associated with the index.

In the example shown in FIGS. 2A and 2B, the visual index display comprises a gauge (dial) 30, with the overall index (40) displayed in the center of the gauge. An outer ring is shaded to provide a visual indication of the index value. The gauge 30 comprises two selectable portions (user selection interfaces). As shown in FIGS. 2A and 2B respectively, the first portion 31 comprises the ring and the second portion 33 comprises an area radially inward from the ring.

As shown in FIGS. 2A and 2B, a pointer 35 may be placed in the first or second portion (user selection interface) of the gauge 30. The selection may be based, for example, on the location of the pointer 35 or the user may click a mouse once the pointer is placed in the specified area. If the visual index display is located on a touch screen, the user may tap on the desired portion. The term 'select' as used herein may refer to any user initiated action, including for example, placing a pointer over a portion of the visual index display, clicking a mouse, entering one or more keystrokes, using a voice command, etc.

Referring now to FIG. 2A, when the user selects the ring (first selection interface portion) 31 and the index is in an abnormal state, the measures that are out of tolerance are displayed to the right of the gauge (indicated at 32). In this example, each measurement in the first set of measurements is shown in its own gauge. If the user places the pointer over the ring 31 (or clicks anywhere within the ring), only measurements that are outside of a defined threshold (e.g., in a top percentile of measurements or fall outside of a defined limit) are displayed. In the example shown in FIG. 2A, only memory and utilization are shown since they are above a specified threshold (e.g., above or equal to 90%, or top 40% of out of tolerance measurements). As described in detail below with respect to FIG. 5, the number of measurements displayed when the user selects the first portion 31 of the gauge 30 may be based on a sensitivity setting for the visual index display.

Referring now to FIG. 2B, when the user selects the second portion 33 of the gauge 40, all measurements (second set) are shown. The measurements shown in FIG. 2A (memory and utilization) are included along with CPU (computer processing unit), bandwidth, and storage (indicated at 34). Rather than showing all measurements when the second portion of the gauge is selected, only a portion of the measurements may be shown (e.g., all measurements outside of a second defined threshold). Any other grouping may be used for the second set of measurements, which include measurements from the first set, and in most cases will include additional measurements.

Figure 3A:
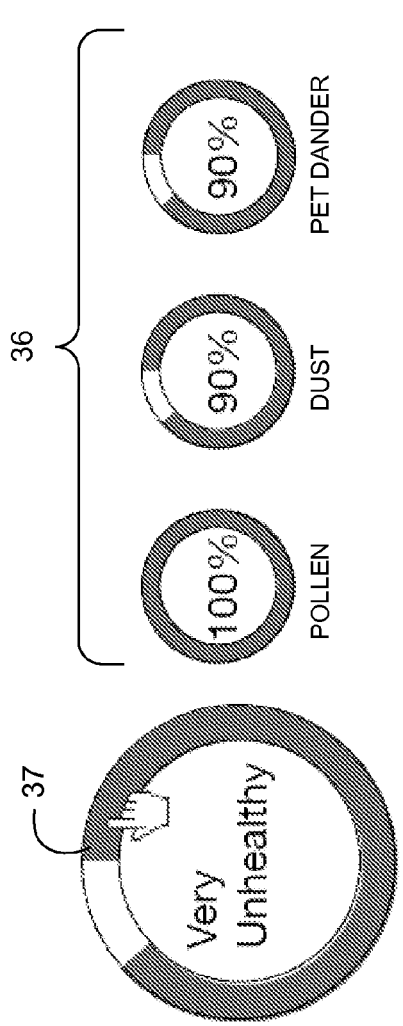
FIGS. 3A and 3B depict other examples of the visual index display, in accordance with one embodiment.
Figure 3B:
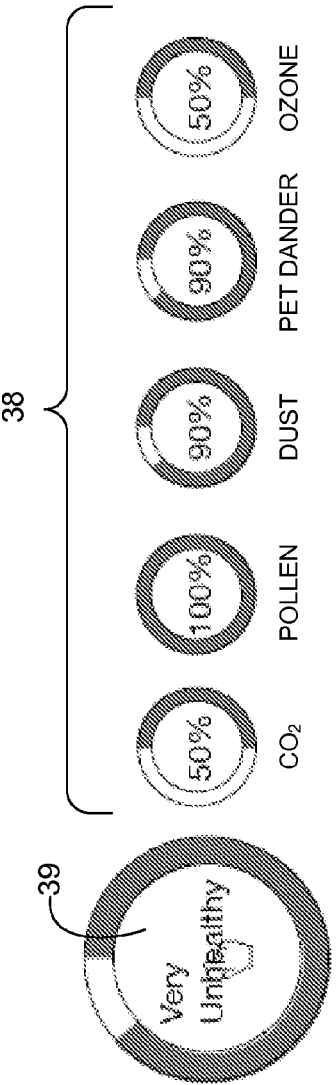

FIGS. 3A and 3B illustrate another example of a visual index display, in accordance with one embodiment. The gauge is used to indicate the air quality of an environment (e.g., room, home, building, factory, etc.). In this example, the index indicates the general health of the air. Rather than having a numerical index value (as shown in FIGS. 2A and 2B), FIGS. 3A and 3B display the term "Very Unhealthy" to indicate the system state. When a first portion 37 of the gauge is selected (FIG. 3A), measurements are shown for pollen, dust, and pet dander (e.g., all measurements equal to or above 90%, or top 60% of out of tolerance measurements) (indicated at 36). In FIG. 3B, a user selects the second portion 39 of the gauge and all measurements are shown ($CO_2$, pollen, dust, pet dander, and ozone) (indicated at 38).

It is to be understood that the visual index displays, indexes, and measurements shown in FIGS. 2A, 2B, 3A, and 3B are only examples and that other types of images or data may be used without departing from the scope of the embodiments.

Figure 4:
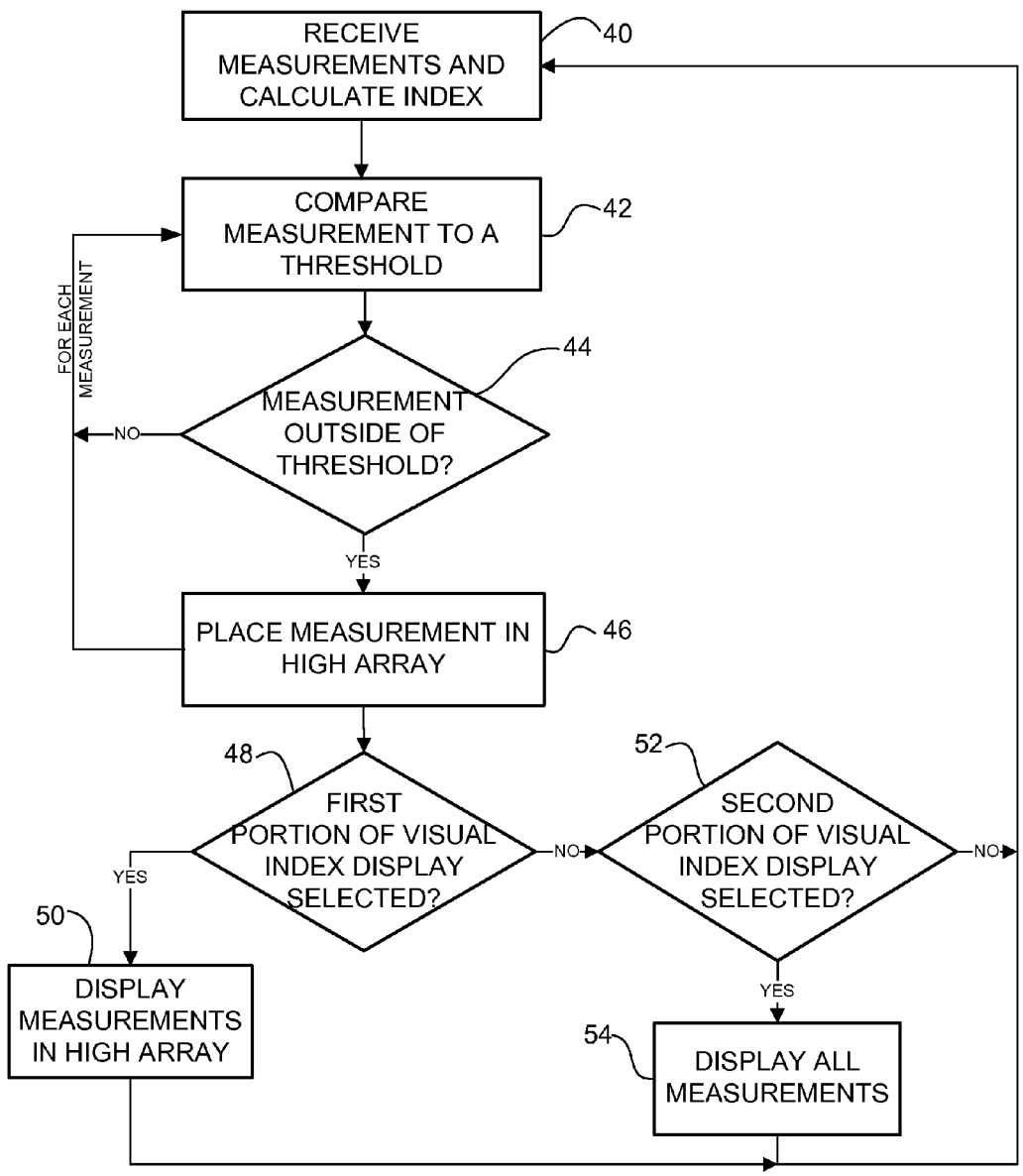
FIG. 4 is a flowchart illustrating an overview of a process for providing visualization filtering for index measures, in accordance with one embodiment.

FIG. 4 is a flowchart illustrating an overview of a process for providing contextual visualization filtering for index measures, in accordance with one embodiment. At step 40, the index module 26 (FIG. 1) receives measurement data and calculates an index. The data may be collected and stored at the network device 10 and periodically updated. For example, the network device 10 may periodically request updates from the monitor (or monitors) 12, or the monitor may send updates to the network device at specified intervals or when one or more of the measurements change or fall out of tolerance. Each measurement is compared to a predefined threshold associated with the measurement (step 42). The threshold may be, for example, a maximum value, a minimum value, a range, or a percent greater than or less than an average or limit.

If the measurement falls outside of the specified threshold, the measurement may be placed in a high array (e.g., table, list, or any suitable data structure) (steps 44 and 46). Steps 42, 44, and 46 may be performed sequentially for each measurement or at the same time for each measurement. If a user selects a first portion of the visual index display (e.g., ring 31 in FIG. 2A), only measurements in the high array (or a subset of measurements in the high array) are displayed (first set of measurements) (steps 48 and 50). As described in detail below, the measurements in the high array may be sorted and based on a configured sensitivity level, only a portion of the measurements may be displayed. If the user selects a second portion of the visual index display (e.g., circle 33 in FIG. 2B), all measurements are displayed (second set of measurements) (steps 52 and 54).

It is to be understood that the process shown in FIG. 4 and described above is only an example and that steps may be added, modified, deleted, or combined, without departing from the scope of the embodiments. For example, the first set of measurements displayed at step 50 may include only a subset of measurements in the high array, and the second set of measurements displayed at step 54 may include the first set of measurements and any number of additional measurements (up to all measurements used to define the index). Also, there may be more than two selectable portions of the visual index display corresponding to additional sets of measurements (e.g., more than one threshold defined).

Figure 5:
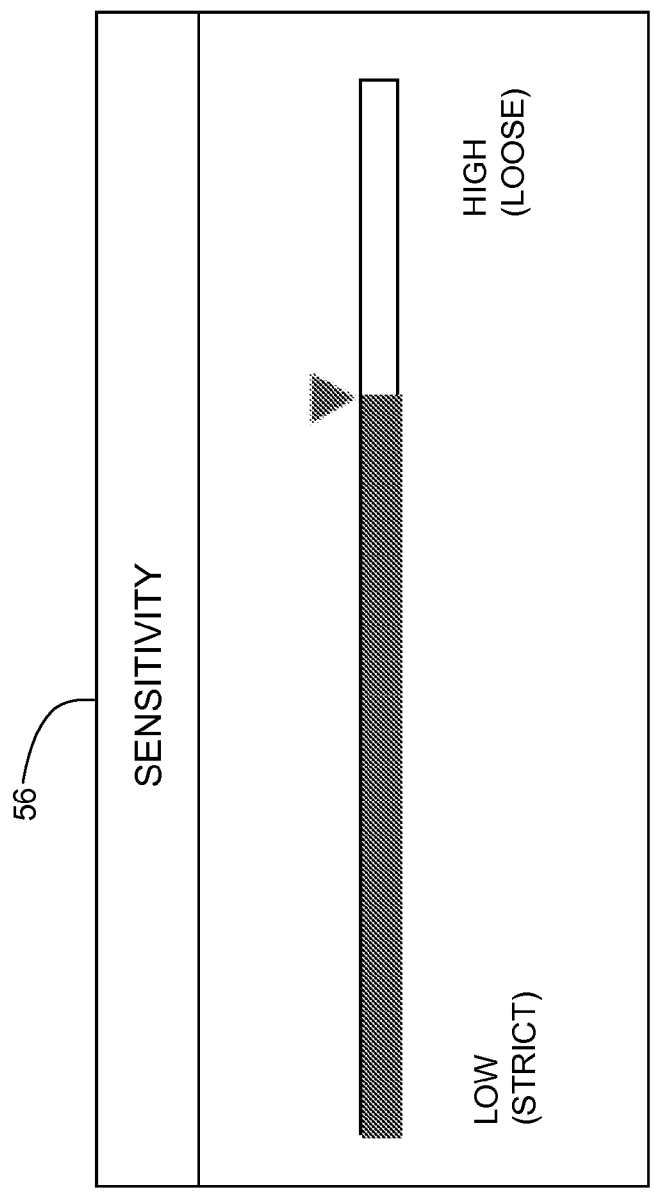
FIG. 5 illustrates a graphical user interface for use in adjusting sensitivity of displayed measurements in FIGS. 2A and 3A, in accordance with one embodiment.

FIG. 5 illustrates an example of a sensitivity graph 56 used to select displayed measurement sensitivity, in accordance with one embodiment. The sensitivity graph 56 allows a user to adjust a sensitivity that controls how many out of tolerance measurements are displayed through ranking of the measurements. In one embodiment, the sensitivity graph 56 is presented as a GUI with the pointer being selectable by a user to define a sensitivity level. Each of the measurements may be normalized so that it can be compared to the other measurements and ranked. For example, the measurement may be adjusted by calculating: abs[(measured value−threshold (or average))/threshold]*100.

In one example, the measurements are divided into n groups (where n is equal to the number of sensitivity levels). The contributing measurements may be ranked and only some of the measurements included in the first displayed set of measurements. For example, X % of the contributors may be included in the first set and shown on the visual index display based on the sensitivity setting (high to low). In one example a low (strict) setting may be used to display only those measurements in the top $90^{th}$ percentile. A middle setting may be used to display those measurements in the top $50^{th}$ percentile, and a high (loose) sensitivity setting may be used to display those measurements in the top $20^{th}$ percentile. The high/loose setting displays a large set of the out of tolerance measurements, while a low/strict setting displays a smaller set of the out of tolerance measurements. In one embodiment, a default sensitivity level may be set to the most sensitive value where all out of tolerance values are displayed. The sensitivity setting further refines the usefulness of the interaction to best meet end user needs based on their specific use case. It is to be understood that the percentiles described above for the sensitivity settings are only examples and that other parameters may be used.

Although the method and apparatus have been described in accordance with the embodiments shown, one of ordinary skill in the art will readily recognize that there could be variations made without departing from the scope of the embodiments. Accordingly, it is intended that all matter contained in the above description and shown in the accompanying drawings shall be interpreted as illustrative and not in a limiting sense.

What is claimed is:

1. A method comprising:
   receiving a plurality of measurements, each of said measurements associated with a different parameter;
   calculating an index based on said measurements; and
   generating a visual index image indicating said index, the visual index image comprising a first portion and a second portion, each of said portions configured for selection by a user;
   wherein a first set of measurements is displayed when said first portion of the visual index image is selected and a second set of measurements is displayed when said second portion of the visual index image is selected, wherein said first set of measurements is a subset of said second set of measurements.

2. The method of claim 1 wherein said first set of measurements comprises one or more of said measurements outside of a specified threshold.

3. The method of claim 1 wherein said second set comprises all of said measurements.

4. The method of claim 1 further comprising ranking a group of said measurements based on an amount each of said measurements is out of tolerance, wherein said first set of measurements comprises a percentile of said ranked measurements.

5. The method of claim 4 wherein said percentile comprises a user configured percentage.

6. The method of claim 1 wherein each of said measurements comprises a value calculated based on a comparison to an average value.

7. The method of claim 1 wherein the visual index image comprises a gauge visually indicating said index.

8. The method of claim 1 wherein said first portion comprises a ring and said second portion comprises an area radially inward from said ring.

9. The method of claim 1 wherein said measurements comprise network monitored measurements.

10. The method of claim 1 wherein said measurements are based on input received at a sensor.

11. An apparatus comprising:
    a processor for calculating an index based on received measurements, each of said measurements associated with a different parameter, and generating a visual index image indicating said index, the visual index image comprising a first portion and a second portion, each of said portions configured for selection by a user; and
    memory for storing said measurements;
    wherein a first set of measurements is displayed when said first portion of the visual index image is selected and a second set of measurements is displayed when said second portion of the visual index image is selected, wherein said first set of measurements is a subset of said second set of measurements.

12. The apparatus of claim 11 wherein said first set of measurements comprises one or more of said measurements outside of a specified threshold.

13. The apparatus of claim 11 wherein said second set comprises all of said measurements.

14. The apparatus of claim 11 wherein said first set of measurements comprises a percentile of out of tolerance measurements ranked based on an amount each of said measurements is out of tolerance.

15. The apparatus of claim 11 wherein each of said measurements comprises a value calculated based on a comparison to an average value.

16. The apparatus of claim 11 wherein the visual index image comprises a gauge visually indicating said index.

17. The apparatus of claim 11 wherein said first portion comprises a ring and said second portion comprises an area radially inward from said ring.

18. The apparatus of claim 11 wherein said measurements comprise network monitored measurements.

19. The apparatus of claim 11 wherein said measurements are based on input received at a sensor.

20. Logic encoded on one or more non-transitory computer readable media for execution and when executed operable to:
 calculate an index based on received measurements, each of said measurements associated with a different parameter; and
 generate a visual index image indicating said index, the visual index image comprising a first portion and a second portion, each of said portions configured for selection by a user;
 wherein a first set of measurements is displayed when said first portion of the visual index image is selected and a second set of measurements is displayed when said second portion of the visual index image is selected, wherein said first set of measurements is a subset of said second set of measurements.

* * * * *